United States Patent [19]

Hartmann et al.

[11] 4,402,949

[45] Sep. 6, 1983

[54] STABLE SOLUTIONS OF HYDROGENATED ERGOTALKALOIDS

[75] Inventors: Volker Hartmann, Nuremberg; Karl-Heinz Otto, Kastl/Opf.; Ludwig Patt, Nuremberg, all of Fed. Rep. of Germany

[73] Assignee: Sandoz Ltd., Basel, Switzerland

[21] Appl. No.: 317,660

[22] Filed: Nov. 2, 1981

Related U.S. Application Data

[63] Continuation-in-part of Ser. No. 298,504, Sep. 1, 1981, abandoned, which is a continuation of Ser. No. 206,529, Nov. 12, 1980, abandoned.

[30] Foreign Application Priority Data

Nov. 12, 1979 [DE] Fed. Rep. of Germany ....... 2945636

[51] Int. Cl.³ .................... A61K 31/725; A61K 31/48
[52] U.S. Cl. .................................... 424/183; 424/261
[58] Field of Search ............................ 424/183, 261

[56] References Cited

U.S. PATENT DOCUMENTS

| | | | |
|---|---|---|---|
| 2,269,145 | 1/1942 | Cutler et al. | 424/261 |
| 3,030,272 | 4/1962 | Schultz | 424/183 |
| 4,069,185 | 1/1978 | Sullivan | 260/29.6 |
| 4,087,567 | 5/1978 | Sullivan | 427/2 |
| 4,090,977 | 5/1978 | Dubin | 252/408 |
| 4,112,925 | 9/1978 | Sullivan | 128/2 |
| 4,138,565 | 2/1979 | Ehrhardt | 544/346 |
| 4,196,196 | 4/1980 | Tiholiz | 424/178 |

OTHER PUBLICATIONS

Bergogne, Revue de l'Atherosclerose, (Paris), 10 (2), 11–13, (1968).
Windsor et al., Nature 190, 263–4, (1961).
Fiedler, Lexikon der Hilfsstoffe 1971, 25–26.
Merck Index, 9th Ed., 1663, (1976).
Sandoz Package Insert—"Heparin-Dihydergot ®".

*Primary Examiner*—Sam Rosen
*Attorney, Agent, or Firm*—Gerald D. Sharkin; Robert S. Honor

[57] ABSTRACT

Stable solutions of (a) hydrogenated ergot alkaloids and (b) heparin as well as the salts thereof in a carrier medium comprising (c) water, (d) a mono- or poly-alcohol, and (e) urea or a pharmaceutically acceptable calcium or magnesium salt or ethylenediaminetetraacetic acid, and combinations thereof.

39 Claims, No Drawings

STABLE SOLUTIONS OF HYDROGENATED ERGOTALKALOIDS

The present application is a continuation-in-part of co-pending application Ser. No. 298,504, filed Sept. 1, 1981, which in turn is a continuation of application Ser. No. 206,529, filed Nov. 12, 1980, and both now abandoned.

The present invention relates to pharmaceutical compositions in the form of stable solutions and comprising as active ingredients a combination of
(a) a compound of formula I,

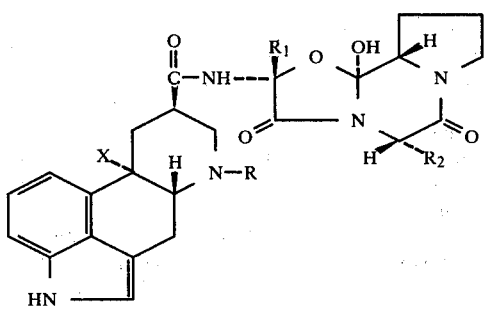

wherein
R is hydrogen or $C_{1-4}$alkyl,
$R_1$ is methyl, ethyl or isopropyl,
$R_2$ is isopropyl, sec.-butyl, isobutyl or benzyl, and
X is hydrogen or methoxy,
or a pharmaceutically acceptable acid addition salt thereof;
and
(b) heparin or a pharmaceutically acceptable salt thereof.

Previous attempts to prepare pharmaceutical compositions in solution form comprising mixtures of active ingredients (a) and (b) as aforesaid (for example of dihydroergotamine (DHE) and dihydroergovaline or their salts, e.g. the methane sulfonate, or of 6-nor-6-isopropyl-9,10-dihydro-2'β-methyl-5'α-benzyl-ergopeptine or its salts, e.g. the maleate, and of heparin or its salts, e.g. the sodium salt) have not met with success. First the individual ingredients are themselves unstable in solution. Secondly, when combined in solution, the ingredients (a) and (b) react to form difficultly soluble salts, e.g. DHE-heparinate, which precipitate out of the solution. The obtained solutions accordingly possess very low stability. They cannot be kept in reserve for periods of more than a few hours and are thus of little practical value.

Various proposals have been made to surmount this problem. Thus it has been suggested to use e.g. the methane sulfonate salt of dihydroergotamine in the form of a solid solution employing polyvinylpyrrolidone. Salt formation can be delayed in this manner, but only for a relatively limited period of time. More recently lyophilised preparations have been developed for use in the preparation of injectable solutions.

As an alternative, individually stabilized solutions comprising components (a) and (b) separately, have been developed. The individually stabilized solutions are then brought into admixture shortly before administration.

Clearly none of these proposals provides a satisfactory, practical answer to the problem. The development of stabilized solution forms comprising ingredients (a) and (b) in combination, having a prolonged shelf-life, capable of transport and storage and ready for use as and when required has remained a major objective.

In accordance with the present invention it has now surprisingly been found that the above problems may be overcome and clear solutions of components (a) and (b) in combination obtained, which are stable over prolonged periods of time, e.g. for two years and more, employing a carrier medium comprising
(c) water;
(d) a pharmaceutically acceptable mono- or polyalcohol; and
(e) urea or a pharmaceutically acceptable calcium or magnesium salt of ethylenediaminetetraacetic acid, or combinations thereof.

Ethylenediaminetetraacetic acid (EDTA) and various of its salts are known to be of use in the treatment of a vari... medical conditions and to be suitable as a component in various compositions for use in the pharmaceutical and related arts [see e.g. Fiedler: "Lexikon der Hilfstoffe für Pharmazie, Kosmetik und angrenzende Gebiete," Cantor KG, Aulendorf i. Würt. (1971) p.p. 25 and 26]. Thus use of EDTA and its salts as a therapeutic de-contaminant and as an anti-coagulant have been proposed in U.S. Pat. No. 3,838,196 and various proposals have been made for the use of EDTA (i) in combination with other EDTA salts as an anti-coagulant mixture for blood, including heparinized blood (U.S. Pat. No. 4,090,977) and (ii) for the preparation of anti-coagulant coating compositions for e.g. analytical equipment (U.S. Pat. Nos. 4,069,185; 4,112,925 and 4,087,567). U.S. Pat. No. 4,196,196 also describes the use of e.g. MgK$_2$EDTA in combination with other pharmaceutically active components, such as insulin, as an ingredient in compositions suitable for enhancing tissue perfusion and re-perfusion. Though this latter patent refers specifically to calcium EDTA, it is stated that this salt is not suitable for use in accordance with the invention. In addition U.S. Pat. No. 4,188,465 discloses the use of EDTA as a stabilizing component in urease compositions comprising urease, glutathione, EDTA and citrate. The above references are illustrative of the art.

The surprising finding that magnesium and calcium salts of EDTA can be used as a stabilizor component in the preparation of stable compositions in accordance with this invention comprising ingredients (a) and (b) in combination, and overcoming the difficulties previously encountered in the art as hereinbefore described, in particular formation of insoluble salts between ingredients (a) and (b), has not however previously been reported.

Accordingly the present invention provides, in a first aspect a pharmaceutical composition in stable solution form comprising as active ingredients a combination of a component (a) and a component (b) as hereinbefore defined and a carrier medium comprising components (c), (d) and (e) as hereinbefore defined.

Preferably the compositions according to the invention have a pH of from 4 to 6.

Suitable pharmaceutically acceptable acid addition salt forms of the compounds of formula I, include e.g. the methane sulfonates, maleates and tartrates. Suitable pharmaceutically acceptable salts of heparin include e.g. the sodium, potassium and calcium salt.

Preferred ingredients (a) are dihydroergotamine or a pharmaceutically acceptable acid addition salt thereof, in particular the methane sulfonate, dihydroergovaline or a pharmaceutically acceptable acid addition salt thereof, in particular the methane sulfonate and 6-nor-6-isopropyl-9,10-dihydro-2'β-methyl-5'α-benzyl-ergotpeptine and the pharmaceutically acceptable acid addition salts thereof, in particular the maleate. When (b) is present in pharmaceutically acceptable salt form this is preferably the sodium salt.

The ingredients (a) and (b) are preferably present in a ratio of 1 mg compound of formula I:500 to 70,000 I.U., more preferably 2,000 to 20,000 I.U. heparin. When ingredient (a) and/or (b) is present in pharmaceutically acceptable salt form the equivalent amount of salt form giving the stated ratios for the free compound is employed.

Components (c) and (d) are preferably present in an amount of 45 to 72% and 28 to 55% respectively based on the total volume of the composition.

Preferred components (d) are ethanol, propylene glycol, polyethylene glycol, suitably polyethylene glycol having an average molecular weight of 400, diethylene glycol, triethylene glycol and glycerol, as well as mixtures thereof. More preferably component (d) comprises a mixture of (i) ethanol and (ii) triethylene glycol or of (iii) glycerol and (iv) propylene glycol. In such mixtures (i) and (ii) are preferably present in a ratio of from 1:6 to 10, more preferably 1:8 parts by weight and (iii) and (iv) are preferably present in a ratio of from 1:8 to 12, more preferably 1:10 parts by weight.

Component (e) comprises (i) urea or (ii) a pharmaceutically acceptable magnesium or, preferably, calcium salt of EDTA or (iii) combinations of ingredients (i) and (ii) as aforesaid. Indicated magnesium and calcium salts of EDTA are the mono-magnesium and mono-calcium salts including the pharmaceutically acceptable polymetal salts incorporating magnesium and, preferably, calcium together with mono-valent metal ions, e.g. sodium or potassium ions. The preferred salt for use in accordance with the invention is the mono-calcium-bis-sodium salt ($CaNa_2EDTA$) also known as calcium titriplex. The mono-magnesium-bis-potassium salt ($MgK_2EDTA$) may also be mentioned. For reasons of physiological tolerability it is preferred to use a salt of EDTA as aforesaid, rather than urea.

Ingredient (e) is preferably present in a range of from about 2 to 20 mg, more preferably 2 to 10 mg, most preferably 2 to 5 mg based on an amount of 5,000 I.U. heparin.

In a preferred embodiment the compositions of the invention also comprise as a further ingredient (f), a physiologically acceptable anaesthetic. As anaesthetic component (f) there may be used any member of the class of physiologically acceptable compounds and substances suitable for use as anaesthetic agents. Preferably however the component (f), when present, is an "acetanilide anaesthetic," by which is meant any member of the class of physiologically acceptable acetanilide derivatives having anaesthetic activity, including the various known anaesthetically active 2-amino-N-phenylacetanilide derivatives. Preferred acetanilide anaesthetics are 2-(diethylamino)-N-(2,6-dimethyl-phenyl)-acetamide (also known as lidocaine), 2-(butylamino)-N-(2-chloro-6-methyl-phenyl)-acetamide (also known as Hostacain) and 2-(2-diethylaminoacetamido)-m-toluic acid methyl ester (also known as Baycain).

The use of anaesthetics in compositions intended for injection is of course known in the art and combinations of components (a) and (b) as hereinbefore described, for example of Hydergine and heparin and dihydroergotamine and heparin, together with an anaesthetic component, e.g. xylocaine or lidocaine are known [see e.g. Bergogne, "Revue de l'Atherosclerose" (Paris), 10(2), pp 11–13 (1968)]. Apart from their clearly advantageous anaesthetic properties e.g. when the compositions are administered by injection, it has surprisingly been found that the presence of an acetanilide anaesthetic as ingredient (f) surprisingly contributes to the long-term stability properties of the inventive compositions as may be demonstrated on storage at elevated temperatures, e.g. of above 50° C., and over longer periods of time, e.g. upwards of 6 months. For the above reasons incorporation of an acetanilide anaesthetic as ingredient (f), while not essential to the obtention of stable solutions in accordance with the invention, is especially preferred. Most preferably ingredient (f), in particular acetanilide anaesthetics as ingredient (f), when present are present in an amount of 1 to 2% by weight based on the total weight of the composition.

The compositions according to the invention may contain further additives, e.g. stabilizing agents, preserving agents, colouring agents and surfactants, as known in the art.

The compositions of the invention are suitably put up in unit dosage form, e.g. in the form of ampoules for injection, including e.g. throw-away syringes containing a predetermined amount of the composition. Such unit dosage forms preferably contain per unit dosage about 0.5 mg compound of formula I or about 2,500 or about 5,000 I.U. heparin. Most preferably they contain about 0.5 mg compound of formula I and about 2,500 or about 5,000 I.U. heparin simultaneously.

In addition to the foregoing the present invention also provides a process for the preparation of pharmaceutical compositions in accordance with the invention, which process comprises bringing an active ingredient (a) and an active ingredient (b) as hereinbefore defined into solution in a carrier medium comprising components (c), (d), (e) and, optionally, (f) as hereinbefore defined.

Preferably the process is carried out step-wise in a procedure comprising (1) preparing a solution of an active ingredient (a) in a solvent medium comprising components (d) and, optionally, (f);

(2) preparing a solution of an active ingredient (b) in a solvent medium comprising components (c) and (e);

(3) combining the solutions obtained via steps (1) and (2); and (4) optionally adding additional component (c) or (d).

The process of the invention is preferably carried out with protective gassing, e.g. $CO_2$-gassing, of the solutions. If the pH of the obtained solution is outside the range pH 4 to 6, it is preferably adjusted to within this range e.g. by the addition of an appropriate quantity of a pharmaceutically acceptable acid e.g. an organic acid. When an acid addition salt of a compound of formula I is employed as ingredient (a), the added acid will preferably correspond to the salt form employed. Thus when ingredient (a) is in methane sulfonate salt form, any adjustment of the pH necessary will preferably be effected by addition of methane sulphonic acid.

The obtained composition may be put-up in unit dosage form as hereinbefore described, e.g. by filling into ampoules after filtration, preferably with protective, e.g. $CO_2$, gassing.

The solutions according to the invention may be used for therapeutic treatment or prophylaxis as known in the art; for example as anti-thrombotic agents particularly in the prophylaxis of post-operative thrombosis as described in e.g. U.K. patent specification No. 1,557,331.

The following examples are illustrative of the present invention.

EXAMPLE I

Preparation of a 5,000 I.U. heparin/0.5 mg Dihydroergotamine injectable solution (1) 18.4 kg of propylene glycol and 1.84 kg of anhydrous glycerol are poured into a 50 liters stirring vessel, and the mixture stirred for 10 minutes with $CO_2$-gassing. 0.0286 kg of dihydroergotamine methane sulphonate and 0.426 kg of lidocain hydrochloride are dissolved in the mixture with stirring and $CO_2$-gassing over a period of a further 30 minutes.

(2) 18.4 kg of water (suitable for injection) are poured into a 30 liters stirring vessel and stirred for 10 minutes with $CO_2$-gassing. 1.896 kg of heparin sodium salt (=ca. 285.7 million I.U.) and 0.114 kg of $CaNa_2EDTA$ hexahydrate (commercially available under the name calciumtitriplex) are then dissolved in the water with stirring and $CO_2$-gassing over a further 30 minutes.

(3) The solution obtained via step (2) above is added with stirring and $CO_2$-gassing to the solution obtained via step (1). The vessel in which solution (2) is obtained is then washed out with 1 kg of water (suitable for injection) and is also added to the step (1) solution. The combined solutions are stirred for a further 10 minutes with $CO_2$-gassing. The pH of the solution is ca. 5.7.

(4) The solution is made up to a weight of 42.810 kg (or 40 liters) by the addition of water (suitable for injection).

(5) The obtained solution is pre-filtered using a membrane-filter (0.2 μm: Ultipor nm. Pall) and then passed via a sterilized pressure-filtration apparatus having a membrane filter (0.2 μm: Ultipor nm. Pall) at 1.7 bar with $CO_2$ directly into an ampoule-filling machine. The solution is filled in 0.8 ml dosages into 1 ml ampoules under sterile conditions.

EXAMPLE II (2,500 I.U. heparin/0.5 mg dihydroergotamine injectable solution)

Steps (1) to (4) of example I are repeated precisely using the following quantities of ingredients:

| | | |
|---|---|---|
| (Step 1) | Propylene glycol | 15.30 kg |
| | Anhydrous glycerol | 1.53 kg |
| | Dihydroergotamine-methane sulphonate | 0.03 kg |
| | Lidocain—$HCl.H_2O$ | 0.32 kg |
| (Step 2) | Water (for injection) | 12.00 kg |
| | Heparin—Na salt | 0.997 kg (= 150 million I.U.) |
| | $CaNa_2EDTA$ (hexahydrate) | 0.12 kg |
| (Step 3) | No change | |
| (Step 4) | The solution is made up to a weight of 32.040 kg (or 30 liters) by the addition of water (for injection). | |
| (Step 5) | The resultant solution is filled into 1 ml ampoules in 0.6 ml dosages. | |

EXAMPLE III (5,000 I.U. heparin/0.5 mg dihydroergotamine injectable solution)

Steps (1) to (4) of example I are repeated precisely using the following quantities of ingredients:

| | | |
|---|---|---|
| (Step 1) | Propylene glycol | 23.0 kg |
| | Anhydrous glycerol | 2.3 kg |
| | Dihydroergotamine-methanesulphonate | 0.0357 kg |
| | Lidocaine—$HCl.H_2O$ | 0.5329 kg |
| (Step 2) | Water (for injection) | 23.0 kg |
| | Heparin—Na salt | 2.1158 kg (= 357,142,800 I.U.) |
| | $CaNa_2EDTA$ (hexahydrate) | 0.1428 kg |
| (Step 3) | No charge | |
| (Step 4) | The solution is made up to a weight of 53.5 kg by the addition of water (for injection). | |
| (Step 5) | The resultant solution is filled into 1 ml ampoules in 0.7 ml dosages - heparin content = 5,000 I.U.. | |

EXAMPLE IV (2,500 I.U. heparin/0.5 mg dihydroergotamine injectable solution)

Steps (1) to (4) of example I are repeated precisely using the following quantities of ingredients:

| | | |
|---|---|---|
| (Step 1) | Propylene glycol | 25.5 kg |
| | Anhydrous glycerol | 2.55 kg |
| | Dihydroergotamine-methane sulphonate | 0.05 kg |
| | Lidocain—$HCl.H_2O$ | 0.533 kg |
| (Step 2) | Water (for injection) | 15.0 kg |
| | Heparin—Na Salt | 1.5334 kg (= 250 million I.U.) |
| | $CaNa_2EDTA$ (hexahydrate) | 0.2 |
| (Step 3) | No change | |
| (Step 4) | The solution is made up to a weight of 53.4 kg by the addition of water (for injection). | |
| (Step 5) | The resultant solution is filled into 1 ml ampoules in 0.5 ml dosages - heparin content = 2,500 I.U.. | |

EXAMPLE V (i) The method of example I is repeated using an equivalent quantity of a 1:10 (parts by weight) mixture of ethanol and triethylene glycol in place of propylene glycol and glycerol in step (1).

(ii) The method of example I is repeated using an equivalent quantity of Hostacain in place of lidocain in step (1).

(iii) The method of example I is repeated using an equivalent quantity of Baycain in place of lidocain in step (1).

(iv) The method of example I is repeated omitting lidocain as ingredient in step (1).

EXAMPLE VI (1) 0.025 g dihydroergotamine methanesulphonate and from 1.066 to 2.13 g lidocain-$HCl.H_2O$ are dissolved with stirring in 2.0 to 3.0 g anhydrous glycerol and 20 to 30 g propylene glycol.

(2) 125,000 to 250,000 I.U. heparin-NaSalt and 0.2 to 0.5 g urea are dissolved with stirring in 53.2 g water (for injection).

(3) The solution obtained from step (2) is added with stirring to the solution obtained from step (1).

(4) The combined solutions are filled in 1.0 ml quantities into 1.5 ml ampoules.

Steps (1) through (4) are performed in an inert atmosphere with nitrogen or $CO_2$-gassing.

We claim:

1. A pharmaceutical composition in stable solution form comprising as active ingredient a combination of (a) a compound of formula I,

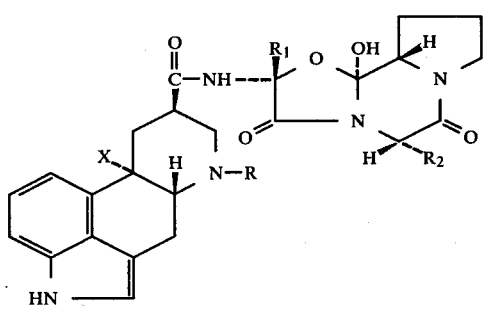

wherein
R is hydrogen or $C_{1-4}$alkyl,
$R_1$ is methyl, ethyl or isopropyl,
$R_2$ is isopropyl, sec.-butyl, isobutyl or benzyl, and
X is hydrogen or methoxy,
or a pharmaceutically acceptable acid addition salt thereof; and (b) heparin or a pharmaceutically acceptable salt thereof, and a carrier medium comprising
(c) water;
(d) a pharmaceutically acceptable mono- or polyalcohol; and
(e) urea or a pharmaceutically acceptable calcium or magnesium salt of ethylenediaminetetraacetic acid, or combinations thereof.

2. Composition according to claim 1, having a pH of from 4 to 6.

3. Composition according to claim 1, wherein the compound of formula I is dihydroergotamine.

4. Composition according to claim 1, wherein the compound of formula I is dihydroergovaline.

5. Composition according to claim 3, wherein the compound of formula I is in the form of the methane sulphonate.

6. Composition according to claim 4, wherein the compound of formula I is in the form of the methane sulphonate.

7. Composition according to claim 1, wherein the compound of formula I is 6-nor-6-isopropyl-9,10-dihydro-2'β-methyl-5'α-benzyl-ergopeptine.

8. Composition according to claim 7, wherein the compound of formula I is in the form of the maleate.

9. Composition according to claim 1, wherein the heparin is in the form of the sodium salt.

10. Composition according to claim 1, wherein the compound of formula I and heparin are present in a ratio of 1 mg:500 to 70,000 I.U.

11. Composition according to claim 10, wherein the ratio is 1 mg:2,000 to 20,000 I.U.

12. Composition according to claim 1, wherein component (c) is present in an amount of from 45 to 72% based on the total volume of the composition.

13. Composition according to claim 1, wherein component (d) is present in an amount of from 28 to 55% based on the total volume of the composition.

14. Composition according to claim 1, wherein component (d) is selected from the group consisting of ethanol, propylene glycol, polyethylene glycol, diethyleneglycol, triethylene glycol, glycerol and mixtures thereof.

15. Composition according to claim 14, wherein component (d) comprises (i) ethanol and (ii) triethylene glycol or (iii) glycerol and (iv) propylene glycol.

16. Composition according to claim 15, wherein (i) and (ii) are present in a ratio of from 1:6 to 10 parts by weight or (iii) and (iv) are present in a ratio of from 1:8 to 12 parts by weight.

17. Composition according to claim 16, wherein (i) and (ii) are present in a ratio of from 1:8 parts by weight or (iii) and (iv) are present in a ratio of from 1:10 parts by weight.

18. Composition according to claim 1, wherein component (e) comprises a pharmaceutically acceptable calcium or magnesium salt of ethylenediamine tetraacetic acid.

19. Composition according to claim 18, wherein the salt is a polymetal salt incorporating calcium or magnesium together with monovalent metal ions.

20. Composition according to claim 19, wherein the salt is $CaNa_2EDTA$.

21. Composition according to claim 1, wherein component (e) is present in an amount of about 2 to about 20 mg based on an amount of 5,000 I.U. heparin.

22. Composition according to claim 21, in unit dosage form, wherein component (e) is present in an amount of from about 2 to about 5 mg based on an amount of 5,000 I.U. heparin.

23. Composition according to claim 1, containing as an additional component (f), a physiologically acceptable anaesthetic.

24. Composition according to claim 23, wherein component (f) is an acetanilide anaesthetic or a pharmaceutically acceptable acid addition salt thereof.

25. Composition according to claim 24, wherein the acetanilide anaesthetic is selected from the group consisting of lidocain, Hostacain and Baycain.

26. Composition according to claim 23, wherein anaesthetic is present in an amount of from 1 to 2% based on the total weight of the composition.

27. Composition according to claim 1 in unit dosage form.

28. Composition according to claim 1 in ampoule form for injection.

29. Composition according to claim 25, containing 0.5 mg of compound of formula I and 2,500 or 5,000 I.U. heparin.

30. Process for the preparation of a pharmaceutical composition according to claim 1, which process comprises the individual steps of:
(1) preparing a solution of an active ingredient (a) in a solvent medium comprising components (d) and, when required, (f);
(2) preparing a solution of an active ingredient (b) in a solvent medium comprising components (c) and (e);
(3) combining the solutions obtained via steps (1) and (2);
(4) optionally adding additional component (c) and/or (d).

31. Process according to claim 30, conducted with protective gassing during solution.

32. Process according to claim 30, wherein the obtained solution is adjusted to pH 4 to 6.

33. A composition according to claim 1, wherein lettered component
(a) represents dihydroergotamine or a pharmaceutically acceptable salt thereof,
(d) represents (i) ethanol and (ii) triethylene glycol or (iii) glycerol and (iv) propylene glycol wherein (i) and (ii) are present in a ratio of from 1:6 to 10 parts by weight or (iii) and (iv) are present in a ratio of from 1:8 to 12 parts by weight, and
(e) represents a pharmaceutically acceptable calcium or magnesium salt of ethylenediaminetetraacetic acid (EDTA), or combinations thereof.

34. A composition according to claim 1, wherein lettered component
(a) represents dihydroergotamine methanesulfonate,
(b) represents heparin-sodium salt,
(d) represents a 1:10 mixture of glycerol and propylene glycol, and
(e) represents $CaNa_2$ EDTA.

35. A composition according to claim 34 wherein components a:b in non-salt forms, are present in a ratio of 1:2,000 to 20,000 I.U., components (c) and (d) are present in an amount of 45–72% and 28–55% volume percent, respectively, and component (e) is present in an amount corresponding to 2–5 mg. per 5,000 I.U. of component (b).

36. A composition according to claim 35 containing 0.5 mg. of (a) and 2500–5000 I.U. heparin.

37. A composition according to claim 34 containing, as an additional component (f), an acetanilide anaesthetic or a pharmaceutically acceptable acid addition salt thereof.

38. A composition according to claim 35 containing, as an additional component (f), an acetanilide anaesthetic selected from the group consisting of lidocain, Hostocain and Baycain.

39. A composition according to claim 11 wherein component (a) is DHE or a pharmaceutically acceptable acid addition salt thereof, component (c) and (d) are present in an amount, based on the total weight of the composition, of from 45–72% and 28–55%, respectively, and component (e) is present in an amount of from about 2 to about 5 mg. based on an amount of 5,000 I.U. heparin present.

* * * * *